United States Patent [19]

Naipawer et al.

[11] Patent Number: 4,517,386

[45] Date of Patent: May 14, 1985

[54] PROCESS FOR THE REARRANGEMENT OF EPOXIDES

[75] Inventors: Richard E. Naipawer, Wallington; Alan J. Chalk, Kinnelon, both of N.J.

[73] Assignee: Givaudan Corporation, Clifton, N.J.

[21] Appl. No.: 609,403

[22] Filed: May 11, 1984

[51] Int. Cl.$^3$ .............................................. C07C 45/58
[52] U.S. Cl. ..................................... 568/483; 502/203
[58] Field of Search ............... 568/450, 483, 384, 485; 502/203

[56] References Cited

U.S. PATENT DOCUMENTS

| | | | |
|---|---|---|---|
| 2,871,198 | 1/1959 | Appell | 502/203 |
| 3,855,303 | 12/1974 | Bishop | 568/384 |
| 4,359,589 | 11/1982 | Brownscombe | 568/618 |
| 4,396,754 | 8/1983 | Brownscombe | 502/202 |
| 4,407,731 | 10/1983 | Imai | 502/203 |
| 4,456,698 | 6/1984 | Brownscombe | 502/202 |

OTHER PUBLICATIONS

Johannes Dale et al., J. Chem. Soc., Chem. Comm. 1976, 295–296.
Bruce Rickborn et al., J. Amer. Chem. Soc. 93, (1971), 1693–1700.
S. Arctander, "Perfume and Flavor Chemicals" vols. I, II, S. Arctander, Montclair, NJ (1969), Monograph Nos.: 833, 1105, 1494, 1592, 2290, 2343, 2397, 3028.

*Primary Examiner*—Natalie Trousof
*Assistant Examiner*—John T. Sullivan
*Attorney, Agent, or Firm*—Robert F. Tavares

[57] ABSTRACT

Terminal epoxides, also known as alpha-epoxides or 1,2-epoxides, are rearranged predominantly to the corresponding aldehydes using a catalyst system consisting of lithium tetrafluoroborate in a polyether solvent.

7 Claims, No Drawings

PROCESS FOR THE REARRANGEMENT OF EPOXIDES

BACKGROUND OF THE INVENTION

The rearrangement of epoxides is well known in the art. It is further known that acid-catalyzed rearrangement results in the formation of carbonyl products, whereas base-catalyzed rearrangement gives rise to allylic alcohols as products. See *J. Org. Chem.* 35, (1970) 1598.

When an acid catalyst is employed, two product-forming pathways are possible as shown in Scheme i. In Path a the internal epoxide bond (i.e., Bond #1) is cleaved and the hydrogen atom migrates from the terminal carbon atom to the internal carbon atom resulting in the formation of aldehyde 1. In Path b the external epoxide bond (i.e., Bond #2) is cleaved and the $R_2$ group migrates from the internal carbon atom to the terminal carbon atom resulting in the formation of ketone 2. If $R_2$ is a hydrogen atom, then the product is a methyl ketone possessing the same carbon skeleton as the reacting epoxide. On the other hand, if the $R_2$ group is a carbon-bearing substituent, then the resultant ketone will possess a rearranged carbon skeleton.

Scheme I

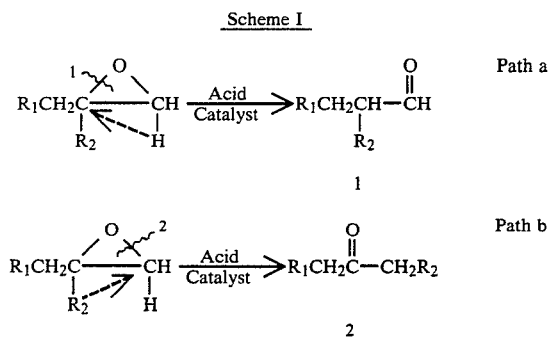

The nature of the $R_2$ group (i.e., its steric bulk, inductive or repulsive electronic effects, etc.), inherent characteristics of the particular epoxide (i.e., ring strain, dipole-dipole interactions, etc.) and the various properties of the acid catalyst will all have an effect on the extent each pathway is followed and the amount of aldehyde and ketone in the final product.

In the case of a 1,2-epoxide where the $R_2$ group is a hydrogen atom and the various steric and electronic effects are minimal, it is difficult to find conditions which cause the rearrangement to occur exclusively by one of the two possible pathways. Known methods using catalysts such as mineral acids or Lewis acids usually give mixtures of aldehydes and ketones.

U.S. Pat. No. 3,855,303 discloses the rearrangement of terminal epoxides to the corresponding aldehydes containing a small amount of the corresponding methyl ketone. The process utilizes alkali metal perchlorates in combination with trialkyl- and triarylphosphine oxides as catalysts for effecting the rearrangement. The commercial feasibility of this process is questionable since no yields are disclosed and since a reaction time of 72 hours is required in the single illustrative example offered.

Organoleptically pure n-aldehydes, such as n-hexanal, n-heptanal, n-decanal, n-dodecanal, etc., are important and very useful ingredients in flavors and fragrances [see S. Arctander, "Perfume and Flavor Chemicals", Vols. I and II, Steffen Arctander, Publisher, Montclair, N.J. (1969)]. None of the processes described in the prior art provides a method of converting terminal epoxides to aldehydes without at the same time producing substantial amounts of ketone or requiring conditions that are not commercially feasible.

Since it is known in the art that terminal epoxides can be produced economically from terminal olefins, most of which are inexpensive and readily available from the petroleum industry, there is a need for an economical and commercially feasible process for converting such epoxides to aldehydes without, at the same time, producing a subatantial amount of the undesired ketone.

THE INVENTION

This invention provides a method for preparing aldehydes of the formula R-CH$_2$CHO, wherein R is a group that is stable under the reaction conditions as defined below, by rearranging the corresponding terminal epoxides in the presence of a catalytic amount of lithium tetrafluoroborate and in the presence of a polyether solvent of the type defined below. The desired aldehydes are provided in good yield without, at the same time, forming substantial amounts of ketone by-product.

More particularly, the 1,2-epoxide to be isomerized can be heated at a temperature of between 80° C. and 200° C. in the lithium tetrafluoroborate-polyether system, to provide a good yield of aldehyde with a high alkanal/alkan-2-one ratio.

The fact that lithium tetrafluoroborate selectively rearranges 1,2-epoxides to aldehydes in good yields is quite surprising in light of prior art which discloses that lithium tetrafluoroborate can be used for bringing about the cyclic oligomerization of ethylene oxide (*J. Chem. Soc., Chem Comm.* 1976, 295).

DESCRIPTION OF THE PREFERRED EMBODIMENTS

The process of this invention can be illustrated as follows

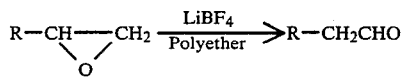

with R and the polyether solvent being as defined herein. Since the invention is directed to the rearrangement of the epoxide to the corresponding aldehyde, the nature of the R group is not critical. inasmuch as the process would work with any R group that was stable under the reaction conditions. As a practical matter, however, the invention would be particularly applicable to those compounds wherein R is a hydrocarbon group, preferably a hydrocarbon group of three carbon atoms or more. While epoxides where R is methyl or ethyl would be suitable, their boiling point is less than the reaction temperatures and would require the use of a pressure reaction vessel to maintain the optimal reaction temperature. There is no maximum limit on the size of the R group, but as a practical matter those epoxides wherein R is less than eighteen carbon atoms are preferred since the olefins from which the larger epoxides would normally be made are less readily available.

Those aldehydes wherein R is an alkyl group having from four to twelve carbon atoms are especially preferred since such aldehydes are of greater commercial importance. While R may be a straight or branched chain alkyl group, those aldehydes wherein R is a straight chain alkyl group are usually of greater importance commercially.

In practicing the process of this invention, the appropriate epoxide is reacted in the presence of the lithium tetrafluoroborate and the polyether solvent at suitable reaction temperature, e.g. 80° C. to 200° C. While the reaction can be run successfully in a number of alternative ways, certain parameters have been determined to be preferred and to provide better yields.

It is preferred to mix the lithium tetrafluoroborate with the polyether solvent, bring this mixture to the desired reaction temperature and add the epoxide to be rearranged to the heated mixture over a period of time. It is suggested, though not proven, that the major side reaction occurs via some sort of polymerization of the epoxide. Adding the epoxide to the reaction mixture slowly over a period of time appears to minimize this side reaction leading to better yields. While the addition time can vary from zero to twenty-four hours, as a practical matter, a six-hour addition time is more than adequate with two to four hours being preferred. Of course, the optimal feed time will depend on the size of the batch, the concentration of the other reagents used and the reaction temperature and it is within the skill of a chemist to determine the optimal time of addition for the reaction size and conditions he desires.

The amount of lithium tetrafluoroborate used is not critical but at least 0.1 weight-percent based on the weight of the epoxide to be reacted is suggested. Amounts above 5.0 weight-percent do not appear to be of any added benefit. As a practical matter, amounts of 1.0 to 2.0 weight-percent per weight of epoxide used are preferred with 1.5 to 1.8 weight-percent being especially preferred.

The presence of the polyether is essential, but the volume is not critical. It is thought, though not proven, that the polyether serves to solvate the lithium ion of the catalyst thus making the anion more available in a manner similar to that observed with crown ethers. Sufficient polyether should be present to do so. As a practical matter, however, it is preferred to use the polyether as the solvent and to use at least one gram of solvent per gram of epoxide used. As a practical matter, there is no benefit in exceeding 20 grams of polyether per gram of epoxide. It is preferred to stay in the range of from about 8:1 to 2:1 with from 3:1 to 5:1 being most practical and especially preferred.

The nature of the polyether is not critical. Any polyoxygenated species such as the dialkyl ethers of glycols and the dialkyl ethers of polyglycols as well as crown ethers should be able to serve as the polyether.

As a practical matter, the commercially available dialkyl ethers of ethylene glycol and polyethylene glycol are preferred with glyme (ethylene glycol dimethyl ether), diglyme (diethylene glycol dimethyl ether) and tetraglyme (tetraethylene glycol dimethyl ether) being readily available. The use of tetraglyme is especially preferred.

As used herein, a polyether will be defined as any compound of the form $R'O-(CH_2-[CH_2]_n-O-)_pR''$ where n can be one or two, p can be one, two, three, four five or six and R' and R'' may be alike or different and be chosen from the group consisting of alkyl radicals of one to four carbons. Preferred are those cases wherein R' and R'' are methyl, n=1 and p=2 through 5 with p=4 being especially preferred.

The temperature affects both the rate and selectivity of the reaction in the expected fashion, i.e. the higher the temperature the faster but less selective the reaction. Below 80° C., the rate is considered to be too slow to be practical, while at above 200° C. the selectivity is considered to be too low to be practical. A temperature range of 90° C. is preferred with a temperature range of 110° C. to 140° C. being especially preferred.

There are other parameters which, although not necessary for the practice of this invention, are beneficial in most instances. For example, in order to minimize any autoxidation of the aldehyde one can add an antioxidant such as butylated hydroxy toluene (BHT), butylated hydroxy anisole (BHA), hydroquinone (HQ), etc., at levels of 0.1 to 0.5 weight-percent. Additionally, the reaction can be carried out under an inert gas atmosphere (e.g., nitrogen, argon, etc.) to suppress autoxidation.

The addition of lithium carbonate has also been found to be beneficial. It is thought, but not proven, that the lithium carbonate serves to neutralize any acid present. Lithium carbonate has a positive affect on the overall yield, but does not affect the aldehyde to ketone product ratio.

THE EXAMPLES

The following examples illustrate the practice of the method of this invention and should not be considered as limiting. Among the methods used to characterize the compositions of the reaction products were the following:
1. Infrared spectra (IR) were recorded as neat samples on a Perkin-Elmer Model 137.
2. Gas-liquid chromatography (GLC) was carried out on a 10% Carbowax 20M ($\frac{1}{4}$ inch I.D.×6 ft.) column and a fused silica Silicone Oil SE-30 capillary column (0.25 mm I.D.×30 meters).
3. Unless otherwise indicated, weights are in grams, temperatures are in degrees centigrade, pressures are in mm Hg and yields are based on theory.

GENERAL PROCEDURE FOR EPOXIDE REARRANGEMENT

The general procedure outlined below typifies the practice of this invention.

Lithium tetrafluoroborate and a suitable antioxidant, if desired, are added to a reaction flask which contains the polyether reaction solvent of choice. The reaction flask is then purged with an inert gas, if desired, and the purge is continued throughout the reaction stage of the process of this invention.

The resultant mixture is stirred and is heated to the desired operating temperature. The apporpriate epoxide is then added to the heated mixture over the time period of choice.

The progress of the rearrangement can be monitored by removing an aliquot (0.5–1.0 ml) from the reaction mixture, quenching the aliquot in water (5.0–10.0 ml) and then subjecting the upper oil layer to GLC analysis. Stirring and heating of the reaction mixture is continued until GLC analysis shows less than 1% of the starting epoxide.

The reaction mixture is then cooled to ambient temperature and is poured into an equal volume of water. The resultant mixture is extracted in the usual manner with hexane or other suitable extraction solvent and the resultant solvent extract is backwashed with water to remove any polyether solvent which may have been carried over in the extraction process.

The solvent extract is concentrated and the product isolated by distillation under the appropriate vacuum.

Examples 1 to 10 of Table 1 illustrate the general procedure.

TABLE I

| EX-AM-PLE | EPOXIDE | (WGT.) | SOL-VENT[a] | WGT. % LiBF$_4$ | WGT. % Li$_2$CO$_3$[b] | REACTION TEMP. | TIME (HRS.) EPOXIDE FEED | TIME (HRS.) ADDITIONAL TIME | ALDEHYDE PRODUCT | YIELD %[c] | ALKANAL[d] / ALKAN-2-ONE |
|---|---|---|---|---|---|---|---|---|---|---|---|
| 1 | 1,2-Epoxy-decane | (46.8 g) | Tetraglyme | 2.1 | 0.0 | 140° | 0.5 | 0.75 | n-Decanal | 38.9 | 17.4/1.0 |
| 2 | 1,2-Epoxy-decane | (46.8 g) | Tetraglyme | 1.6 | 0.0 | 120° | 1.5 | 2.25 | n-Decanal | 46.8 | 23.1/1.0 |
| 3 | 1,2-Epoxy-decane | (46.8 g) | Tetraglyme | 1.6 | 0.0 | 120° | 3.0 | 1.25 | n-Decanal | 53.4 | 25.8/1.0 |
| 4 | 1,2-Epoxy-decane | (46.8 g) | Tetraglyme | 1.6 | 0.2 | 120° | 1.5 | 2.25 | n-Decanal | 51.1 | 24.8/1.0 |
| 5 | 1,2-Epoxy-decane | (46.8 g) | Tetraglyme | 1.6 | 0.2 | 120° | 3.0 | 1.75 | n-Decanal | 57.1 | 25.6/1.0 |
| 6 | 1,2-Epoxy-decane | (46.8 g) | Glyme | 1.6 | 0.2 | 90° | 3.0 | 3.25 | n-Decanal | 35.7 | 29.3/1.0 |
| 7 | 1,2-Epoxy-decane | (46.8 g) | Tetraglyme | 2.2 | 0.4 | 140° | 0.5 | 1.0 | n-Decanal | 46.8 | 18.5/1.0 |
| 8 | 1,2-Epoxy-decane | (46.8 g) | Tetraglyme | 2.0 | 0.5 | 120° | 3.0 | 0.5 | n-Decanal | 49.4 | 22.8/1.0 |
| 9 | 1,2-Epoxy-dodecane | (55.2 g) | Tetraglyme | 1.7 | 0.5 | 120° | 3.0 | 0.5 | n-Dodecanal | 48.7 | 22.9/1.0 |
| 10 | 1,2-Epoxy-tetradecane | (63.6 g) | Tetraglyme | 1.5 | 0.4 | 120° | 3.0 | 0.5 | n-Tetradecanal | 48.4 | 26.1/1.0 |
| 11[e] | 1,2-Epoxy-decane | (46.8 g) | Tetraglyme | 1.6 | 0.0 | 120° | 0.5 | 2.25 | n-Decanal | 34.0 | 10.8/1.0 |

[a]Volume, 200 ml.; Tetraglyme is tetraethylene glycol dimethyl ether; Glyme is ethylene glycol dimethyl ether.
[b]Lithium carbonate added as a buffering agent.
[c]Yields calculated as percent of theory on epoxide used.
[d]The alkanal/alkane-2-one ratios were determined by glc analysis on a 25 mm (I.D.) × 30 meter fused silica Silicone Oil SE-30 capillary column using a temperature program of 100° → 200° C. @ 10°/min.
[e]Triphenylphosphine oxide (Ph$_3$PO) added at 1.6 Wgt %.

Examples 4 to 10 utilize lithium carbonate as a buffering agent in amounts of 0.2 to 0.5 weight-percent. The addition of lithium carbonate in amounts of up to 5.0 weight-percent is considered beneficial but not essential to the practice of the invention.

Example 11 shows the effect of the addition of triphenyl-phosphine oxide on the reaction system. This oxide, a substance known in the art to be powerful co-catalyst, has a significant detrimental effect on the aldehyde to ketone ratio (see Examples 2 and 11).

We claim:

1. A process for the preparation of an aldehyde of the formula R—CH$_2$CHO wherein R is an alkyl group of from three to eighteen carbon atoms which comprises adding an epoxide of the formula

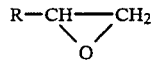

to a mixture of lithium tetrafluoroborate and a polyether at a temperature between 80° C. and 200° C. and isolating the aldehyde formed therefrom.

2. A process according to claim 1 wherein:

(a) The amount of lithium tetrafluoroborate is 0.1 weight-percent to 5.0 weight-percent of the epoxide used, (b) the polyether used has the formula R'O—(CH$_2$—CH$_2$—O—)$_p$R" wherein R' and R" are alike or different and represent an alkyl group of from one to four carbon atoms and p equals one to six, and (c) the weight of polyether is from one to twenty times the weight of epoxide.

3. A process according to claim 1 wherein:

(a) the amount of lithium tetrafluoroborate is between 1.0 and 2.0 weight-percent of the epoxide used, (b) the polyether is CH$_3$—O—(CH$_2$—CH$_2$—O—)$_p$CH$_3$ wherein p equals from one to four, (c) the weight of polyether is from two to eight times the weight of epoxide, and (d) the temperatture is 90° C. to 150° C.

4. A process according to claim 1 wherein:

(a) the amount of lithium tetraflouroborate is between 1.5 and 1.8 weight-percent of the epoxide used, (b) the solvent is tetraglyme in a weight three to five times the weight of epoxide used, and (c) the temperature is between 110° C. and 140° C.

5. A process according to claims 2, 3 or 4 wherein R is an alkyl group having four to twelve carbon atoms.

6. A process according to claim 2, 3 or 4 wherein the epoxide is fed in slowly over a period of from one to six hours.

7. A process according to claim 6 wherein R is a straight chain alkyl group.

* * * * *